United States Patent [19]

Austin, Jr.

[11] 4,188,976
[45] Feb. 19, 1980

[54] MULTIPLE DENTAL HANDPIECE CONTROL SYSTEM

[76] Inventor: George K. Austin, Jr., P.O. Box 209, Rte. 2, Box 254, Newberg, Oreg. 97132

[21] Appl. No.: 878,026

[22] Filed: Feb. 15, 1978

[51] Int. Cl.$^2$ .................. F15B 11/20; F15B 13/08
[52] U.S. Cl. ........................ 137/637.1; 91/189 A; 137/596.14; 433/28
[58] Field of Search ......... 32/22; 91/189 R, 189 A; 137/596.14, 596.18, 637.1

[56] References Cited

U.S. PATENT DOCUMENTS

| | | | |
|---|---|---|---|
| Re. 28,649 | 12/1975 | Austin | 32/22 |
| 3,757,421 | 9/1973 | Kraft | 32/22 |

*Primary Examiner*—Gerald A. Michalsky
*Attorney, Agent, or Firm*—Klarquist, Sparkman, Campbell, Leigh, Hall & Whinston

[57] ABSTRACT

The specification discloses a multiple dental handpiece control system in which lifting one handpiece out of its hanger blocks supply of power and coolants to all other handpieces. Each handpiece has an individual control unit and a blockout unit. When a handpiece is lifted from its hanger, it actuates a valve to cause a piston in its control unit to shift to a condition causing supply of power and coolant fluid to that handpiece and cutting off power to the corresponding pistons in the other control units thereby preventing supply of power and coolant fluids to the other handpiece.

5 Claims, 3 Drawing Figures

MULTIPLE DENTAL HANDPIECE CONTROL SYSTEM

DESCRIPTION

This invention relates to improved multiple dental handpiece control system and has for an object thereof the provision of a new and improved multiple dental handpiece control system.

Another object of the invention is to provide a multiple dental handpiece control system in which a first handpiece lifted out of its holder prevents operation of other handpieces until the first handpiece is returned to its holder.

A further object of the invention is to provide a multiple dental handpiece control system in which a plurality of handpieces are supplied with drive air and coolant fluids from individual modular control blocks, each block having a blocking diaphragm control valve which is closed by pressure from air through an associated control cylinder valve when the associated handpiece is in its hanger to actuate a hanger valve to keep the associated cylinder in one condition, the hanger valve serving, when the associated handpiece is lifted from its hanger, to change the associated cylinder to a second condition permitting operation of that handpiece and that cylinder also cutting off actuating air to the other cylinders when in its second condition.

Figure 1:
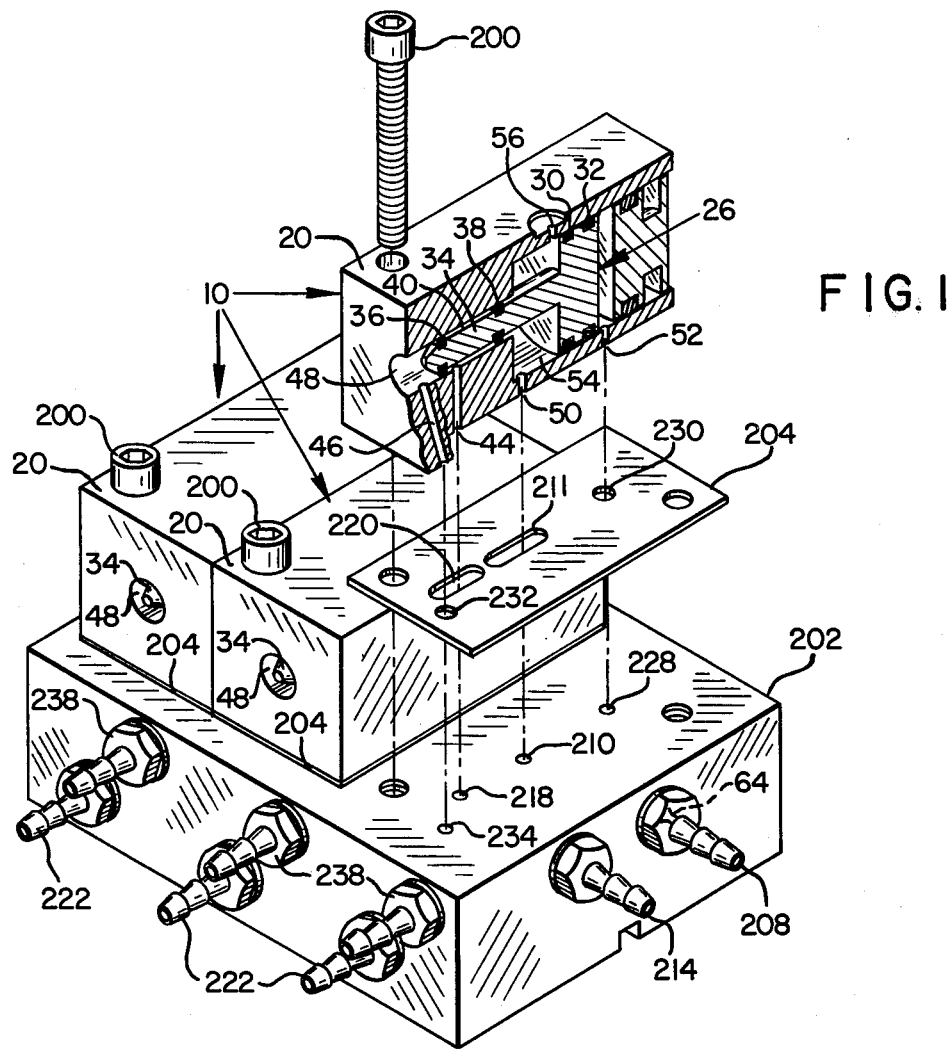
FIG. 1 is a partially exploded, perspective view of a portion of an improved multiple dental handpiece control system forming one embodiment of the invention.
Figure 3:
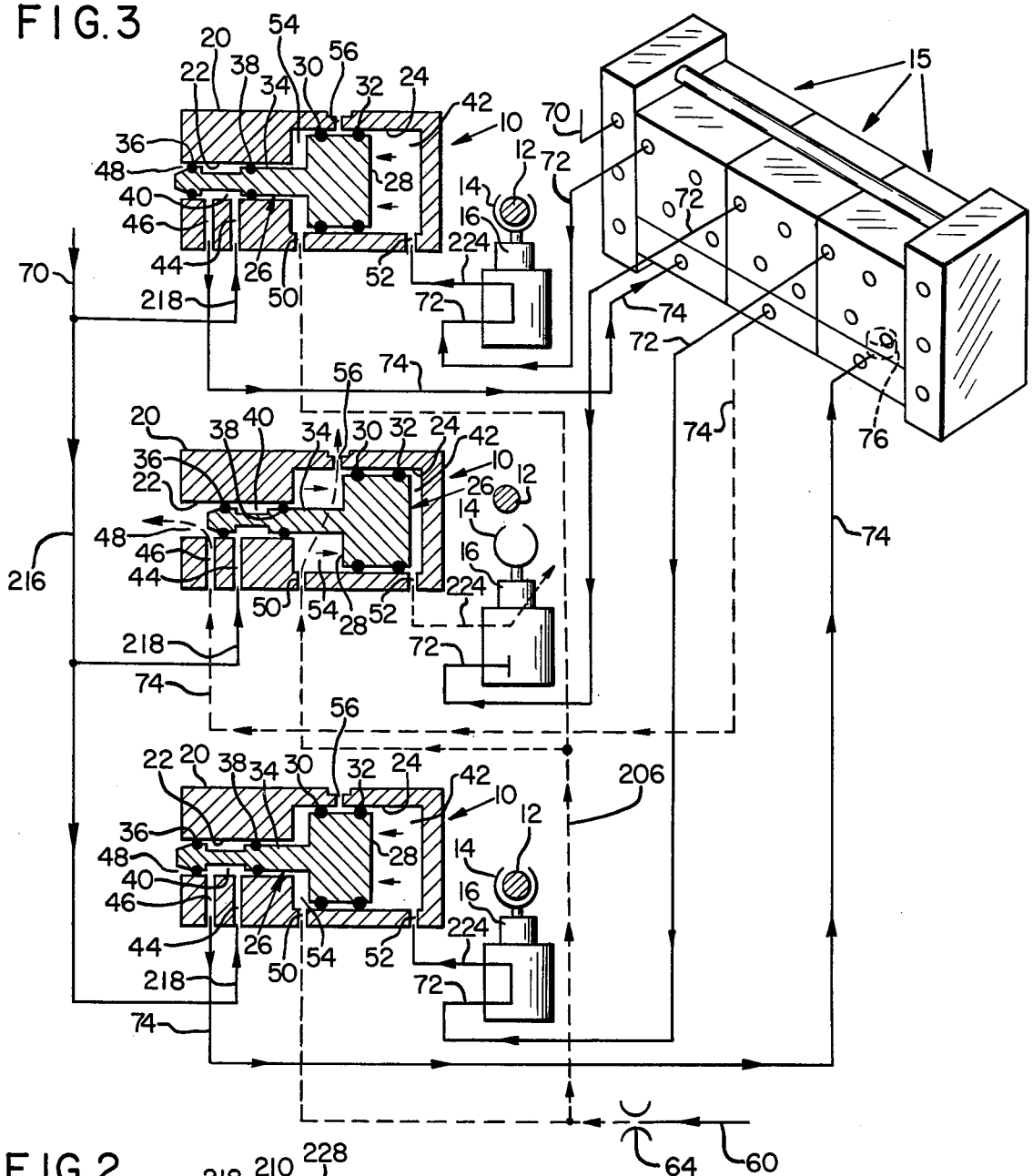
FIG. 3 is a partially sectional, partially perspective, schematic view of the system of FIG. 1.

An improved dental handpiece control system includes a plurality of valve units 10, one for each handpiece 12. The system includes holders or hangers 14 for holding the handpieces, each of which, when in its holder, actuates its hanger valve assembly 16 to prevent operation of that handpiece. The handpiece that is first taken from its holder 14 prevents operation of any handpiece subsequently removed from its holder until the first taken handpiece is returned to its holder. Each handpiece is supplied with drive air, coolant water and coolant air through one of a plurality of module control blocks 15 under the control of the hanger block assemblies 16. The construction and operation of the control blocks is identical to the construction and operation of the control blocks disclosed and claimed in my U.S. Pat. No. 3,638,310.

Each valve unit 10 includes a body 20 having a bore 22 and a counterbore 24. A piston 26 has a head 28 sealed by O-rings 30 and 32 and has a rod or stem 34 sealed in the bore 22 by O-rings 36 and 38. The piston, the bore and the O-rings form cavities or chambers 40, 54 and 42. The smaller diameter cavity 40 has leading thereto an inlet hole 44, an outlet hole 46 and a vent 48 (conveniently the open end of the bore). The larger diameter counterbore 24 (the control cavity) has two holes 50 and 52, one at either end, which serve as ports, alternately inlet and outlet, for the control air. The portion piston rod 34 has the seal rings 36 and 38 spaced such that the end ring 36 passes back and forth across the outlet hole 46 to connect the hole 46 either to vent 48 or inlet 44. The second seal ring 38 seals the small diameter cavity 40 from the large diameter cavity 54.

The large diameter portion or head 28 carries the seal rings 30 and 32 which separate the counterbore 24 into the cavity 42 and cavity 54. Bleeder or vent hole or port 56 leads to the cavity 54 and a hole or port 52 leads into the cavity 42. As can be seen, introducing compressed air into chamber 54 through hole 50 will cause an unbalanced force on head 28 to move the piston to connect outlet hole 46 to vent 48. Relieving the air through hole 56 and pressurizing cavity 42 through hole 52 causes piston 26 to move to the left, as viewed in FIG. 1, to connect outlet 46 and inlet 44. Equal pressure (either zero psi or higher) on either side of piston head 28 does not tend to move the piston. However, there is a small force component toward the stem 34 due to the reduced piston area caused by the stem. This force component is much smaller than the friction force of the seal rings 30, 32, 36 and 38 so movement does not occur. A low pressure air supply line 60, of, for example, twenty pounds per square inch, may be used to control the valves 10 and perform the logic function necessary to allow the first handpiece out (lifted from its hanger) to operate and exclude all other handpieces from operation. In this system, holes 50 in all valve bodies are connected in parallel to a common supply source, a line 60 carrying low pressure air and a restrictor 64. The supply line 60 is equipped with a low volume restrictor 64 to allow the pressure at holes 50 to approach zero psi when any of the vent holes 56 are open. This also limits the venting air volume and slows the pressurizing time of holes 50 when the vents 56 are closed. When all vents 56 are closed, the pressure in cavity 54 slowly increases to the low pressure of line 60. A high pressure line 70 is connected by a passage through control blocks 15 to lines 72 connected to hanger block assemblies 16.

Figure 2:
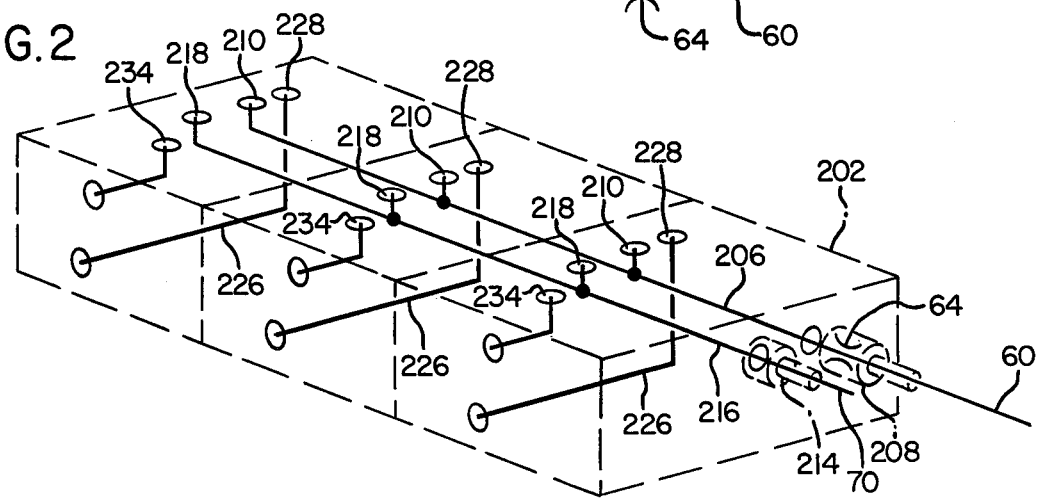
FIG. 2 is a schematic view of a portion of the system of FIG. 1.

As best shown in FIGS. 1 and 2, the valve units 10 may comprise a plurality of the cylinders 20 (with the pistons 26 therein) secured by screws 200 to common manifold 202 with gaskets 204 therebetween. The manifold has a bore 206 supplied with the low pressure air from line 60 through a flow restrictor barb or connector 208. Ports 210 from the bore 206 lead to the ports 50 through holes 211 in the gasket 204. High pressure air is supplied from the line 70, which is connected to a barb or connector 214 leading to a bore 216 having ports 218 connected to the ports 44 through holes 220. Barbs 222 connected to lines 224 from the valves 16 are connected to bores 226 leading to ports 228 leading to the ports 52 through holes 230 in gaskets 204. The ports 46 are connected to the lines 74 through holes 232 in the gaskets, ports 234 in the manifold, bores 236 in the manifold, and barbs or connectors 238.

OPERATION

With all handpieces 12 in their respective holders 14, cavities 42 through holes 52 are pressurized. This pressure causes all stems 34 to move until holes 44 and 46 are common and outlets 46 are pressurized. Pressurizing all of the outlets 46 causes all lines 74 to be pressurized to actuate valves 76 to block supplies of air and water to all the handpieces. In each the cavity 42 pressurizes through hole 52 to a pressure higher than in cavity 54 so that the pistons 26 do not move and thus are kept in their extreme lefthand positions. Removing one handpiece 12 from its holder relieves the pressure in cavity 42. This unbalances the forces on piston 26 such that the piston moves to the right to open port 46 to vent 48. Also, port 56 is opened and reduces the pressure in all cavities 54 to near zero psi. Only a small amount of air can bleed through restrictor 64, less than that permitted by the vents 56. Hence, when one of the other handpieces is removed from its hanger, it relieves the pressure in cavity 42, but since the pressure in each cavity 54 was previously reduced to near zero, the piston does not move, and pressure is maintained in the port 46 of the valve associated with the later removed handpiece. To reset the system and allow operation of a different handpiece, the "FIRST-OUT" handpiece must be replaced in its hanger. Replacing this handpiece in its holder activates its associated valve unit 10 pressurizing the cavity 42 causing piston 26 to connect inlet 44 and outlet 46, which pressurizes outlet 46, closing vent port 56 and pressurizing all the cavities 54.

What is claimed is:

1. In a multiple tool control system,
a plurality of cylinder drives each including a cylinder having a head end and a rod end and a piston having a head and rod movable in the cylinder,
each cylinder having a first port in the head end, a second port in the rod end and an exhaust port intermediate the ends of the cylinder and connected to the second port when the piston is at the head end and blocked by the piston from the second port when the piston is at the rod end,
a plurality of valve means, one for each cylinder drive, normally individually supplying fluid under pressure to the first ports to pressurize the head ends of the cylinders to urge the pistons toward the rod ends and each valve means operable when actuated to exhaust the head end of the cylinder associated therewith,
and limited flow low fluid pressure supply means connected in common to the second ports for driving the pistons from the rod ends to the head ends whenever the head ends are exhausted, whereby when one of the head ends is exhausted, the piston in that cylinder is moved to the head end to exhaust the rod end and thereby exhaust the rod ends of all the other cylinders.

2. The system of claim 1 wherein each cylinder has a long rod bore having a pair of ports spaced therealong, each rod fitting loosely in the rod bore,
and a pair of O-ring seals on the rod and spaced apart to form a barrel valve with the rod bore and the pair of ports.

3. The system of claim 2 wherein one of the O-ring seals on the rod blocks the pair of ports when the piston is at the head end of the cylinder and opens the pair of ports to each other when the piston is at the rod end of the cylinder.

4. The system of claim 3 wherein each of the valve means is a dental handpiece hanger valve.

5. The system of claim 1 wherein each of the valve means is a dental handpiece hanger valve.

* * * * *